(12) United States Patent
Sauter-Starace et al.

(10) Patent No.: US 7,945,336 B2
(45) Date of Patent: May 17, 2011

(54) PROBE WITH MULTIPLE ARMS AND SYSTEM FOR DEEP ELECTRICAL NEUROSTIMULATION COMPRISING SUCH A PROBE

(75) Inventors: Fabien Sauter-Starace, Seyssinet-Pariset (FR); Alim Louis Benabid, Meylan (FR); Patrice Caillat, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 322 days.

(21) Appl. No.: 12/000,835

(22) Filed: Dec. 18, 2007

(65) Prior Publication Data

US 2008/0161896 A1 Jul. 3, 2008

(30) Foreign Application Priority Data

Dec. 18, 2006 (FR) .................................. 06 11022

(51) Int. Cl.
*A61N 1/00* (2006.01)
(52) U.S. Cl. .................................................. 607/116
(58) Field of Classification Search .................. None
See application file for complete search history.

(56) References Cited

U.S. PATENT DOCUMENTS

| | | | |
|---|---|---|---|
| 6,512,958 B1 | 1/2003 | Swoyer et al. | |
| 6,684,109 B1* | 1/2004 | Osypka | 607/122 |
| 7,006,859 B1* | 2/2006 | Osorio et al. | 600/378 |
| 2002/0062143 A1 | 5/2002 | Baudino et al. | |
| 2002/0116042 A1 | 8/2002 | Boling | |
| 2004/0199235 A1 | 10/2004 | Younis et al. | |
| 2005/0075681 A1* | 4/2005 | Rezai et al. | 607/48 |
| 2005/0171558 A1 | 8/2005 | Abovitz et al. | |
| 2005/0267347 A1 | 12/2005 | Oster et al. | |
| 2006/0069417 A1* | 3/2006 | Farley et al. | 607/101 |
| 2006/0122677 A1* | 6/2006 | Vardiman | 607/116 |
| 2006/0129203 A1 | 6/2006 | Garabedian et al. | |
| 2006/0276866 A1* | 12/2006 | McCreery | 607/116 |

FOREIGN PATENT DOCUMENTS

EP 1 062 973 12/2000

OTHER PUBLICATIONS

A.L. Benabid et al. "Long-term suppression of tremor by chronic stimulation of the ventral intermediate thalamic nucleus" (1991), *The Lancet*, vol. 337, pp. 403-406.
H.S. Mayberg et al. "Deep Brain Stimulation for Treatment-Resistant Depression" (2005), Neuron, vol. 45, pp. 651-660.

(Continued)

*Primary Examiner* — George Manuel
*Assistant Examiner* — Robert N Wieland
(74) *Attorney, Agent, or Firm* — Clark & Brody

(57) ABSTRACT

Probe (1) for deep electrical neurostimulation, and more specifically for deep brain electrostimulation, comprising:
   a tubular body (10) of biocompatible material with a lateral wall (11) defining a lumen (12) and a closed anterior end (13), said tubular body (11) can be introduced for at least a part of its length inside a patient's body for reaching a region to be stimulated;
wherein it also comprises:
   a plurality of electrically insulating arms (32) each bearing at least one electrode (40) and being able to pass from a first position in which they are housed inside of said tubular body (11) to a second position in which they project radially from this latter and inversely; and
means (20 and 50) for making said arms (32) pass from said first position to said second position and inversely.

31 Claims, 3 Drawing Sheets

OTHER PUBLICATIONS

A.L. Benabid et al. "Therapeutic electrical stimulation of the central nervous system" (2005), Comptes Rendus Biologies, vol. 328, pp. 177-186.

"Medtronic—DBS Lead Kit for Deep Brain Stimulation 3387-3389-Implant Manual" from Medtronic Inc., downloadable from the Internet site: http://www.medtronic.com/physician/activa/downloadablefiles/197928_b_006.pdf.

M. Leonardi et al. "New Method for Noninvasive Intraocular Pressure monitoring through a Sensing Contact Lens" (2004). *European Glaucoma Society*.

* cited by examiner

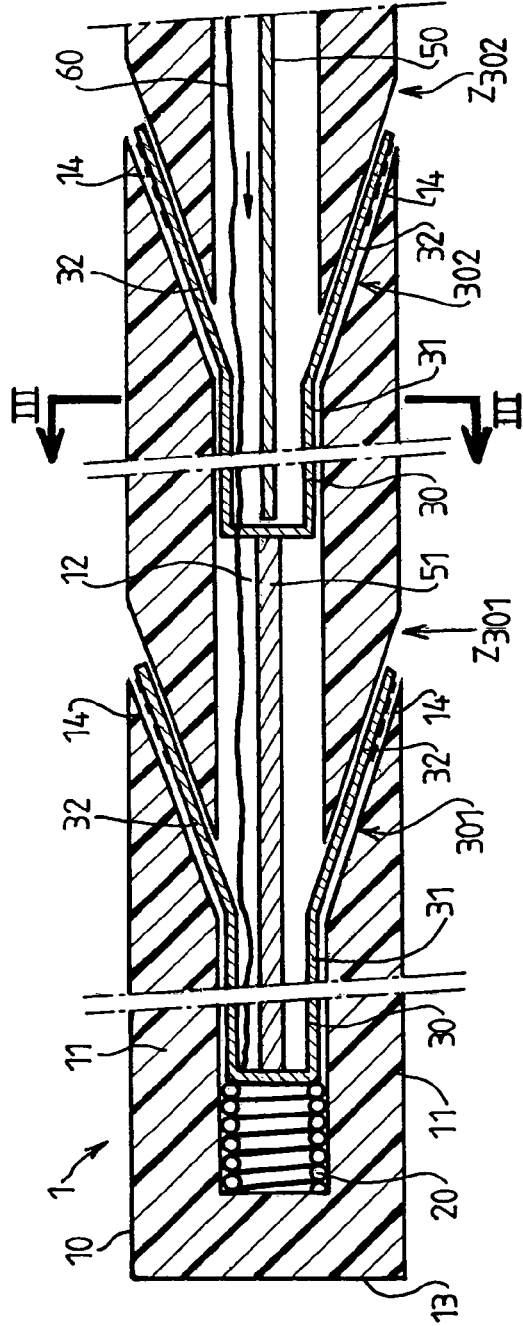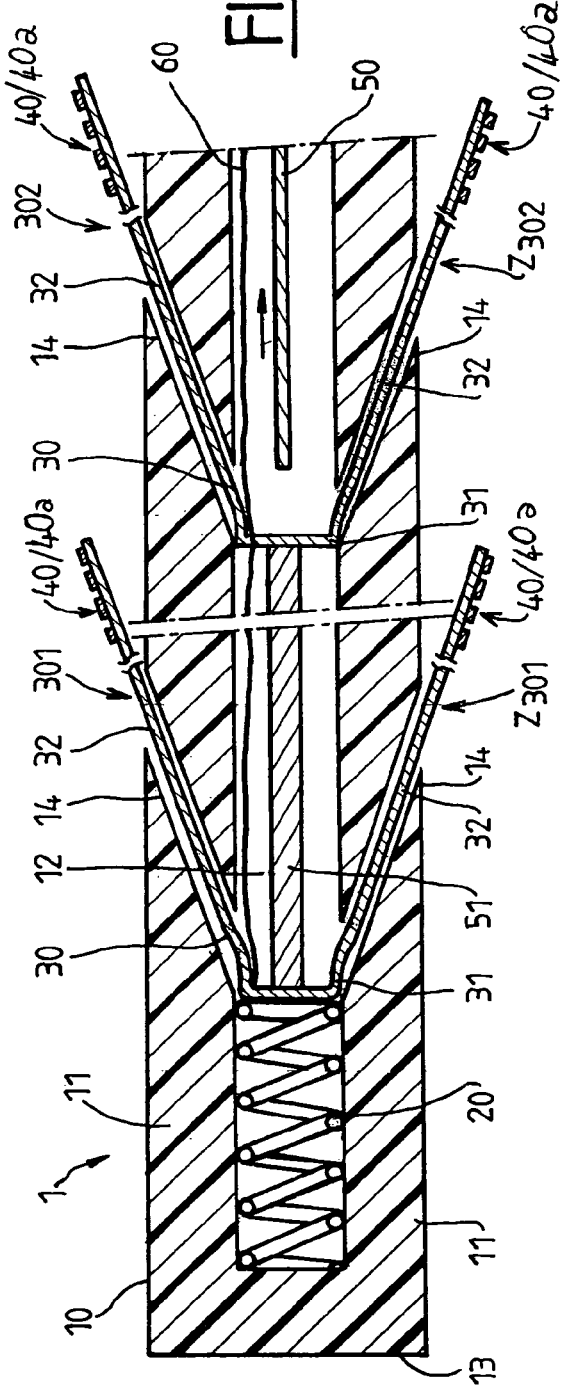

PROBE WITH MULTIPLE ARMS AND SYSTEM FOR DEEP ELECTRICAL NEUROSTIMULATION COMPRISING SUCH A PROBE

This application claims priority from French patent application no. 06111022 filed on Dec.18, 2006, which is incorporated by reference in its entirety.

The invention covers a probe for deep electrical neurostimulation, and more specifically for deep brain electrostimulation. The invention also covers a system for deep electrical neurostimulation comprising at least one such probe.

Deep brain stimulation is a therapeutic technique comprising the implantation of a medical device known as a brain stimulator, which sends electrical pulses to specific parts of the brain. For example, the stimulation of thalamus or hypothalamus nuclei can be used for treating motor disorders such as tremors, caused in particular by Parkinson's disease (see article by A.-L. Benabid, P. Pollak, C. Gervason, D. Hoffmann, D.-M. Gao, M. Hommel, J.-E. Perret and J. de Rougemont: "Long-term Suppression of Tremor by Chronic Stimulation of the Ventral Intermediate Thalamic Nucleus" The Lancet, Volume 337, Number 8738, Feb. 16, 1991, Pages 403-406), and stimulation of the subgenual cingulate cortex is used experimentally for the treatment of particularly severe and treatment-resistant forms of clinical depression (H. S. Mayberg et al. "Deep Brain Stimulation for Treatment-Resistant Depression", Neuron, Vol. 45, pages 651-660, Mar. 3, 2005). Stimulating the posterior hypothalamic nucleus for treating cluster headaches, the periaqueductal gray matter for attenuating pain, and the ventral-median hypothalamus for handling certain cases of obesity is also considered (A.-L. Benabid, B. Wallace, J. Mitrofanis, C. Xia, B. Piallat, V. Fraix, A. Batir, P. Krack, P. Pollak et F. Berger, "Therapeutic Electrical Stimulation of the Central Nervous System" Comptes Rendus Biologies, Volume 328, Number 2, February 2005, Pages 177-186).

In all cases, a deep brain stimulation intervention comprises the insertion in the patient's cranium of a supple probe, guided by a cannula and/or rigid stylus until the point of said probe reaches the region of the brain to be stimulated. In the area of its point, the probe comprises electrodes (generally four), which are connected by a subcutaneous cable to an impulse generation device implanted in turn under the patient's skin like a conventional cardiac stimulator. The cannula and/or stylus are extracted from the patient's cranium after having served the introduction of the probe, whereas this latter remains in place for a period which can reach several years.

A more detailed description of the procedure for implantation of a deep brain stimulation probe is provided by the document "Medtronic—DBS™ Lead Kit for Deep Brain Stimulation 3387 3389—Implant Manual" from Medtronic Inc., downloadable from the Internet site:
http://www.medtronic.com/physician/activa/downloadablefiles/197928_b_006.pdf.

Conventional type probes for deep electrical neurostimulation are described, for example, in the aforementioned document from Medtronic, and also in the document U.S. Pat. No. 6,512,958.

The rectilinear shape of the probe is imposed by the requirement of making its insertion the least traumatic possible for the patient. However, it has the defect of only enabling the stimulation of a very small region of brain tissue, whereas, in order to obtain a better effectiveness of the treatment, it would be desirable to be able to act on a larger volume target, to have more choice of the zone(s) to stimulate over a single trajectory of the probe, or to be able to spatially surround a zone of the patient's brain. The implantation of several probes targeting distinct points of a single target region of relatively significant volume is possible but carries a multiplication of risks and collateral effects from the intervention.

The document EP1062973 describes a supple probe for deep brain electrostimulation intended to be introduced in the brain of a patient using a cannula. The head end of this probe is made up of four pliable stems each provided with an electrode for stimulation and intended to be separated from each other when said head end leaves the cannula. In this manner, it is possible to stimulate a volume of nerve tissue having a tetrahedral shape. The major drawback of this device is that the deployment mode by pliable stems by mutual separation is likely to cause significant irreversible lesions of the brain tissue to be stimulated.

The document US 2005/0267347 describes a stimulation and measurement probe comprising a rigid insertion cannula and one or several flexible electrodes intended to be introduced in the brain of a patient by said insertion cannula. The end of the cannula has a shape suited for separating the said flexible electrode(s) in such a way that the part of these electrodes which goes past said end has an angle of inclination relative to the axis of this latter. Only a limited number of electrodes can be introduced using a single cannula. Furthermore, the flexion mechanism of the electrodes by the end of the cannula does not enable orienting said electrodes independently of each other. Further, this device is intended to be used for performing an exploration step in order to determine the optimal positioning of the stimulation probe, but is not suitable as a deep brain electrostimulation probe because it cannot be implanted to stay.

The purpose of the invention is therefore to obtain a probe for deep electrical neurostimulation making it possible to stimulate a more significant region of nerve tissue than a rectilinear probe and not having the drawbacks of the aforementioned prior art. In particular, a probe according to the invention must be able to be implanted to stay and in a relatively non-traumatic manner for the patient.

Conforming to the invention this object is achieved by a probe for deep electrical neurostimulation comprising: a tubular body of biocompatible material, with a lateral wall defining a lumen, said tubular body can be introduced for at least part of its length inside a patient's body for reaching a region to be stimulated; a plurality of arms each bearing at least one electrode and being able to pass from a first position in which they are housed inside of said tubular body to a second position in which they are made to project radially from the lateral wall of this latter and inversely; and means for making said arms pass from said first position to said second position and inversely, wherein a plurality of said arms are connected together by a base element of tubular shape placed inside of the lumen of said tubular body.

According to particular embodiments of the invention:
all the arms projecting from said lateral wall from a single axial position of this latter can thereby be connected together by a single tubular-shaped base element placed inside the lumen of said tubular body;
said arms and said base element can constitute a single part of strap shape, wound so as to adapt to the shape of the lumen of said tubular body. Said strap can have a thickness between 10 and 100 μm, and preferably between 12 and 50 μm;
a plurality of said arms can project from said lateral wall from a single axial position of this latter.

Said probe can include a plurality of groups of arms, the arms of each group projecting from said lateral wall from a single axial position of this latter and each of said groups corresponding to a different axial position;

said arms can be evenly distributed around the lateral wall of said tubular body;

said arms can be housed at least in part in the channels extending in the lateral wall of said tubular body, preferably along an oblique direction relative to the axis of this latter;

said means for making said arms pass from said first to said second position can include a spring arranged so as to exert on said arms a force directed parallel to the axis of said tubular body, so as to push them to the outside of this latter through said channels;

said arms can be flexible, and are arranged so as to pass from said first to said second position and inversely by translational movement;

according to a first variant, said means to make said arms pass from said second to said first position can include a stem which can be actuated in compression for exerting a force opposed to that of said spring so as to make said arms return into said tubular body through said channels. In particular, said stem can be a stylus which can be introduced in the lumen of said tubular body to make it rigid in order for its insertion in a patient's body;

according to a first variant, the means to make said arms pass from said second to said first position can include a cable which can be actuated in traction for exerting a force opposed to that of said spring so as to make said arms return into said tubular body through said channels;

a plurality of said arms can be connected together by a base element of tubular shape placed inside of the lumen of said tubular body;

said arms can be made of an electrically insulating material and each have at least one electrode on its respective surface. In particular, said arms can be made, at least in part, from a biocompatible insulating material chosen from among the polyimides, and in particular polyisoindroquinazorindiones (PIQ) and the polyimide Pi2611, and the benzocyclobutenes (BCB);

at least one of said arms can also comprise at least a measurement electrode having a smaller surface than that of said stimulation electrodes. In particular, a plurality of measurement electrodes can be disposed near to each stimulation electrode;

such a probe may include electrically conducting elements extending into the lumen or inside of the lateral wall of said tubular element and forming electrical contacts with the electrodes carried by said arms;

the electrodes can be planar electrodes connected to said electrically conducting elements by means of planar conducting tracks formed on said arms;

said conducting elements can extend to an end referred to as posterior of said tubular body and include means for connection to an electrical pulse generator for deep electrical neurostimulation;

said tubular body can be made of a biocompatible material chosen from among silicones, siloxanes, polyurethane and polyvinyl chloride. It can have a predominantly cylindrical shape with a diameter between 500 µm and 5 mm, and preferably between 500 µm and 2 mm;

the total number of arms can be between 3 and 60, and preferably between 4 and 40;

said arms can have a length between 0.2 and 3 mm and preferably between 0.4 and 2 mm; and the length of the tubular body of the probe can be between 15 cm and 40 cm.

Another object of the invention is a system deep electrical neurostimulation comprising an electrical pulse generator for deep electrical neurostimulation; and at least one probe such as described above, whose electrodes are electrically connected to said electrical pulse generator.

Were at least an arm of said probe comprises at least a measurement electrode having a smaller surface than that of said stimulation electrodes, said system may also comprise a measurement instrument electrically connected to said measurement electrodes.

Other properties, details and advantages of the invention will emerge from reading the description made in reference to the attached drawings given as examples and which show, respectively:

FIG. 1 is a longitudinal section view of the anterior end of a probe for deep electrical neurostimulation according to a first embodiment of the invention, in its folded back position for insertion;

FIG. 2 is a longitudinal section view of the anterior end of this same probe in its unfolded position;

Figure 6:
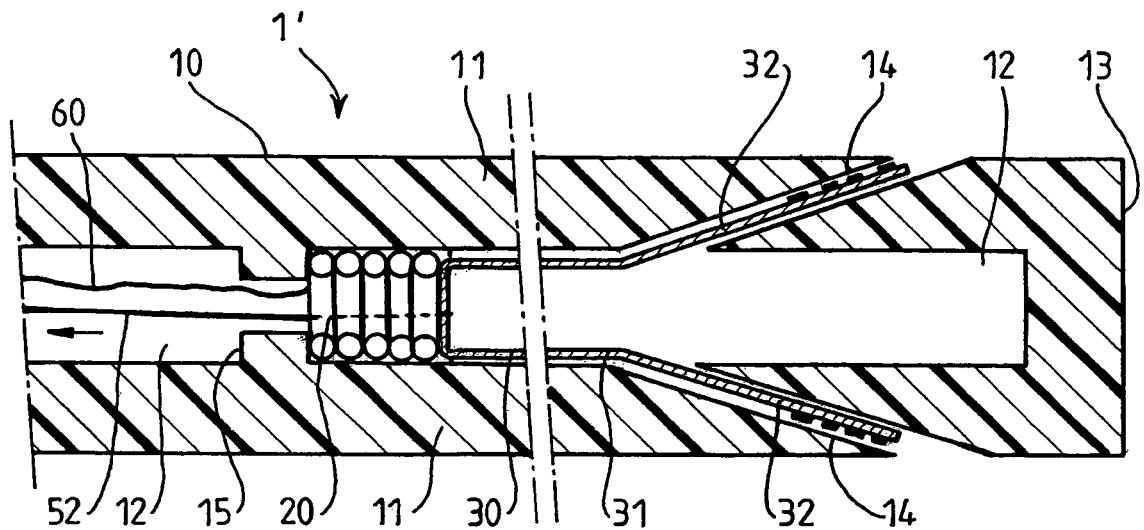
Figure 7:
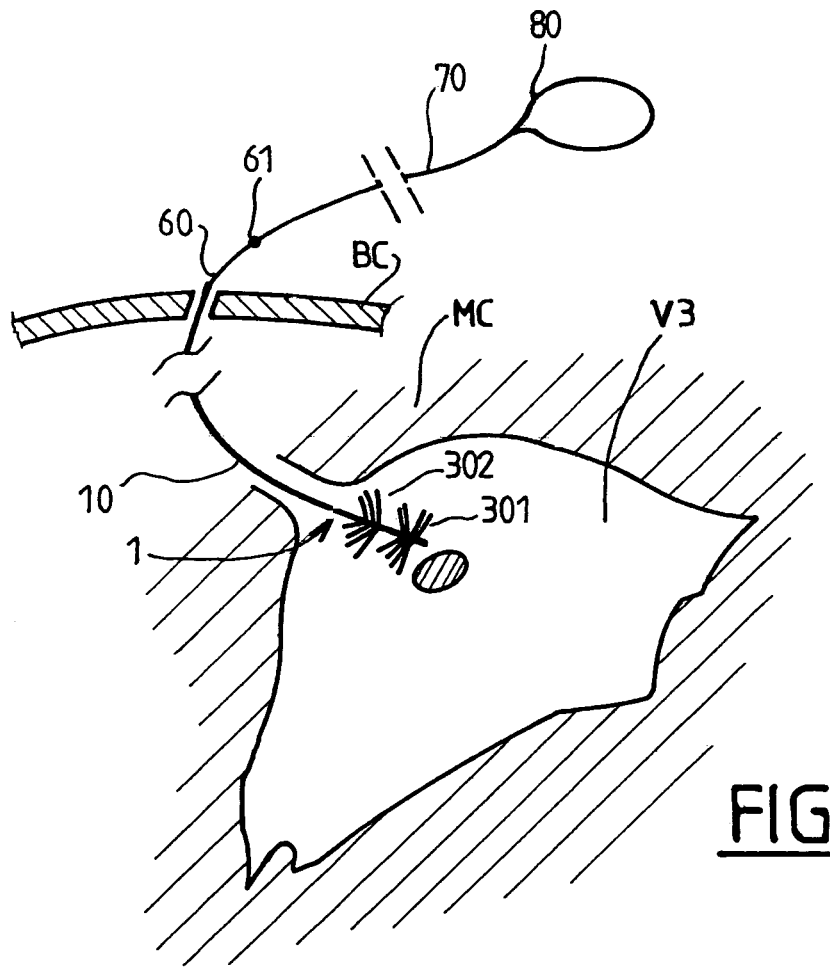

FIG. 6 is a longitudinal section view of the anterior end of a probe for deep electrical neurostimulation according to a second embodiment of the invention, in its folded back position for insertion; and FIG. 7 is an outline sketch of the Deep Electrical neurostimulation System including a probe according to said first embodiment of the invention, introduced in the third ventricle of the brain of a patient.

As shown by FIGS. 1 and 2, a probe 1 according to a first embodiment of the invention comprises a tubular body 10 made of supple biocompatible material having a lateral wall 10 defining a lumen 12 and a closed anterior end 13, forming a point by which the probe can be introduced in the body of a patient, for example in their brain. Typically the probe 1 can be manufactured by molding with an insert being used to obtain a tubular shape.

The tubular body 10 has a substantially cylindrical shape, with a diameter between 0.5 and 5.5 mm approximately, and preferably between 0.5 and 2 mm, such that its insertion in a human brain (or, if applicable, in other nerve tissue such as the spinal cord) does not cause serious lesions; its length is typically of the order of 15 cm to 40 cm according to the implantation protocols.

Any supple biocompatible material can be used for manufacturing a probe according to the invention. In particular, silicones, siloxanes, polyurethane and polyvinyl chloride can be cited.

A spring 20 is housed in the lumen 12 of the tubular body 10 bearing on the inner side of the closed end 13 of the latter; it is understood that the material making up the tubular body 10, although generally defined as "supple", will need to have sufficient rigidity for providing a sufficient rest for the spring 20. The spring 20 is represented in its compressed position in the FIG. 1 and in its extended position in FIG. 2. Although the FIGS. 1 and 2 show a spiral spring, that in no way constitutes a limitation. As a variant it will be possible to use for example, a leaf spring or even a simple block of foam or elastomer. The spring 20 could be made up of metal, for example XC80 type high yield strength stainless steel, a more axially flexible polymer than the tubular body 10, or even a photosensitive polymer. In this latter case, the spring 20 could be manufactured by photolithography or by rapid prototyping.

Two parts 30 are housed so they can slide inside the lumen 12 of the tubular body 10 and so they can be moved by the spring 20 when this latter moves from its compressed position (FIG. 1) to its released position (FIG. 2). Each part 30 comprises a base element 31 of substantially cylindrical shape, full or hollow, and a plurality of arms 32 extending in an axial direction opposite the spring 20 from the periphery of said base element 31.

The two parts 30 are connected to each other by a rigid insert 51 enabling the transmission of an axial displacement inside the lumen 12 of the tubular body 10.

Figure 3:
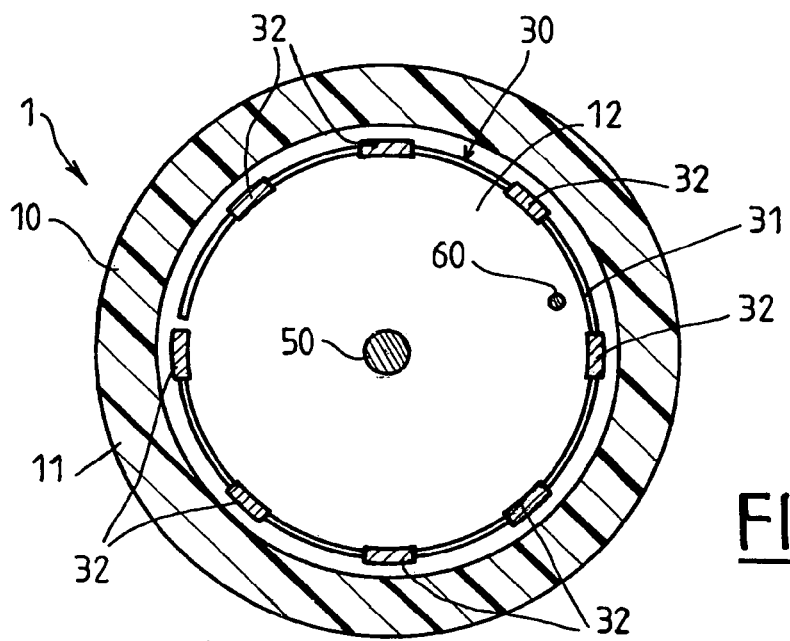
FIG. 3 is a transverse section view along the line 111-111 this same probe in folded position.
Figure 4:
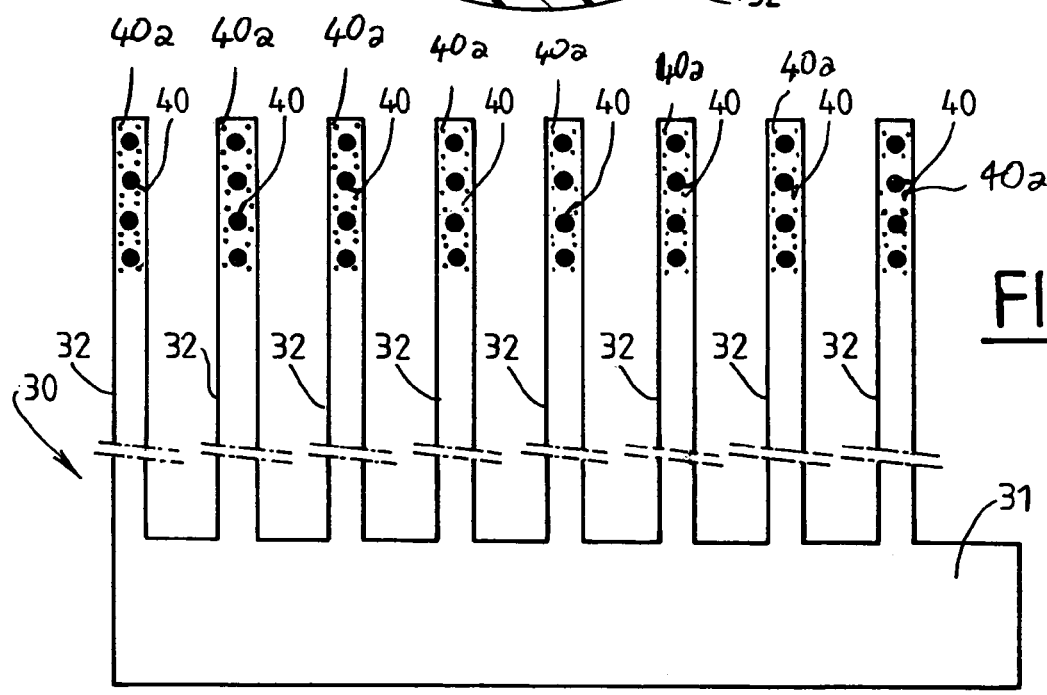
FIG. 4 is the strap-shaped part making up the unfoldable arms of the probe, shown in the un-rolled state.
Figure 5:
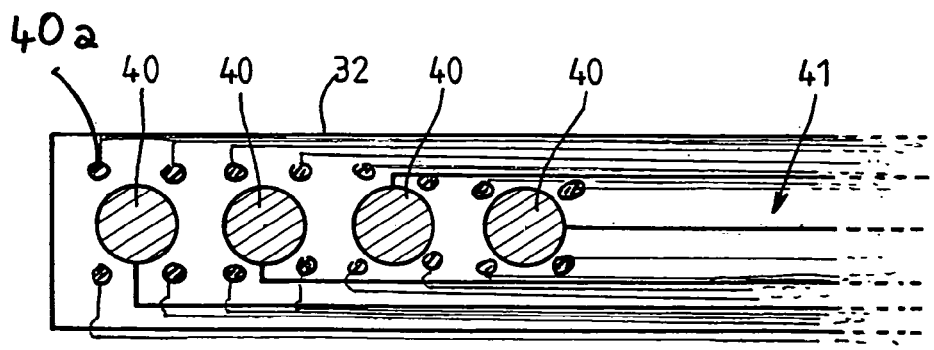
FIG. 5 is an enlarged view of one of the arms of the probe.

As shown in FIGS. 3 and 4, each part 30 can be made up by a strap cut out so as to form a plurality of long shaped arms 32 connected to each other by the base element 31 in band shape and extending perpendicularly to this latter. The strap has a thickness typically between 12 μm and 50 μm, and is wound for being introduced in the lumen 12 of the supple tubular body 10, as illustrated by FIG. 3. FIGS. 3 and 4 show a part comprising eight arms, but it is only meant as an example; the number of arms 32 of each part 30 can typically be between 3 and 12 and preferably between 4 and 8, the number of parts 30 can be between 1 and 5.

Each of the parts 30 forms a group of arms, indicated by the reference numbers 301 and 302. The arms 32 belonging to a single group project from the lateral wall 11 of the tubular body 10 in correspondence from a single axial position $Z_{301}$, $Z_{302}$; each group of arms corresponds to a different axial position. In this manner, when the arms 32 are located in their unfolded position, the probe 1 according to the invention takes a configuration which is reminiscent of that of an umbrella (if only one group of arms is present) or a pine tree (if several groups are provided). Preferably, the arms 32 are evenly distributed around the lateral wall 11 of the tubular body 10.

Each of the arms 32 has planar stimulation electrodes 40, typically four, which are used for applying electrical pulses generated by a stimulation device to the targeted brain tissue. Measurement electrodes 40a, having smaller surfaces than measurement electrodes 40, may also be provided near the latter. Typically, four measurement electrodes can be provided for each stimulation electrode.

Recording electrodes in the vicinity of stimulation electrodes can be used to help the localization of the target. In particular, in the surgical treatment of the Parkinson's disease, the target—the subthalamus nuclei—is localized on the one hand by X ray and RMI imaging routine and on the other hand by electrophysiological recordings around the expected target. The probe described in this invention enable the implantation of the probe by the aforementioned imaging processes, the deployment of the arms and eventually to perform the electrophysiological exploration of the area in order to locate accurately the best stimulation target.

For other diseases, such as epilepsy, these recording electrodes enable the detection of a seizure. Then the implantable pulse generator addresses the stimulation electrode with a stimulus designed to stop the seizure.

These electrodes 40, along with the planar tracks 41 bringing said electrical pulses to these electrodes can be made by conventional techniques for semiconductors or printed circuits, for example by a process of evaporation or sputter deposition or electro deposition (chemical vapor deposition CVD or physical vapor deposition PVD) for the conducting layers followed by etching and spin coating or physical vapor deposition (PVD) for the insulating layers. Other suitable techniques for realizing said planar tracks comprises using conductive inks, sintered powders (obtained, in particular, by laser sintering) and full-plate deposition followed by laser ablation.

The strap from which the part 30 is made must be made up of a material which is electrically insulating, biocompatible and sufficiently flexible to enable it to be wound up. In particular, it may involve a material chosen from among the polyimides, and in particular polyisoindroquinazorindiones (PIQ) and the polyimide Pi2611, and the benzocyclobutene. The polyamides are particularly well-suited because they lend themselves well to photolithography and are currently used in electronics. Release processes known from the prior art enabling in particular the creation of a flexible assembly made up of a conducting layer and two insulating layers of polymer by using a chromium-aluminium sacrificial layer, the anodic dissolution of aluminium enable the release of the stack. These methods are described in particular in the article by Leonardi, P. Leunberger, D. Bertrand, S. Nielsen, A. Bertsch and Ph. Renaud, "Novel Noninvasive Method for Intraocular Pressure Monitoring using Pressure Sensing Contact Lens", European Glaucoma Society '04, Florence, May 30-Jun. 4, 2004.

The electrical pulses for neurostimulation are brought to the conducting tracks 41 of the arms 32 by conducting elements 60, such as metallic cables, extending in the lumen 12 from the tubular body 10 or the inside of its lateral wall 11 to its open posterior end.

The different conducting elements of the probe 1 can be made in metal, ITO (indium aluminum oxide) or graphite. The conducting elements intended to be in contact with the patient's body tissues, such as the electrodes 40, must of course be made of a biocompatible materials such as platinum.

The dimensions of the electrodes 40 are determined as a function of the intended stimulation current knowing that it is not desirable to exceed the current density of 1 mA/mm$^2$, by analogy with the values currently used in deep brain electrostimulation with conventional type probes. Typically, measurement electrodes can have a surface comprised between 400 μm$^2$ and 6 mm$^2$.

The arms 32, with a length typically between 0.2 and 3 mm, are entirely housed inside of the tubular body 10 when the spring 20 is located in its compressed state (first position, FIG. 1). More precisely, the arms 32 extend for most of their length inside of the lumen 12, but their ends are housed in the oblique channels 14 oriented in a direction opposite to that of the point 13 of the probe. Advantageously, the channels 14 make an angle between 10° and 90°, and preferably between 20° and 45° with the axis of the tubular body 10.

In this way, when the spring releases (second position, FIG. 2) it pushes the arms 32 toward the outside of the probe 1 through said oblique channels 14. Thus, the electrodes 40 placed at their ends can contact brain tissue regions relatively distant from the axis of the probe and stimulate a target region of relatively large volume.

The reversibility of the movement is important for enabling the probe 1 to be extracted without damaging tissue more than would the probe 1 alone.

As the arms 32 do not go past the perimeter of the tubular body 10 during the insertion and extraction of the probe, these operations are no more traumatic for the patient than if the conventional probe were used. However, the volume of the region stimulated can be much larger.

The actuation of the spring 20 to make the arms 32 pass from their first position to their second position and inversely is made possible by a rigid stylus 50 traversing the lumen 12 of the tubular body. Such a stylus, made for example from metal, is generally provided in the probes for electrical neurostimulation known from the prior art in order to make the supple tubular body rigid so as to allow its insertion. In the case of the invention, when the probe 1 is introduced in the patient's skull, the stylus 50 compresses the spring 20 and keeps the arms 32 in their first folded position. Once the probe 1 has reached its final emplacement, the stylus 50 is extracted which makes it possible for the spring 50 to expand and make the arms 32 pass into their second unfolded position. To enable an extraction of the probe 1 without danger, it is necessary to again introduce the stylus 50 in the tubular body 11 in order to again fold the arms 32.

Globally, the arms 32 complete a pure translational movement to move from their first to their second position and inversely, which makes it possible to minimize the damage to the tissue to be stimulated. It involves a major advantage of the invention relative to the device from the aforementioned document EP1062973. This translational movement is done the length of the trajectory comprising an elbow at the transition between the lumen 12 and the channels 14. It is understood that the arms must be sufficiently supple for being able to deflect in the area of this elbow, and at the same time sufficiently rigid for being able to overcome the resistance opposing their deployment by the target tissue. However, in certain cases it will be possible to perform this deployment in a cavity filled with cerebrospinal fluid, for example the third ventricle which is adjacent the thalamus and hypothalamus which are conventional target regions for brain electrostimulation.

To enable the assembly of the different elements of the probe 1, and in particular the introduction of the spring 20 and the moving parts 30 in the lumen 12 of the tubular body 10, it is preferable that the closed end 13 of said probe 1 be made up of a removable cap.

FIG. 6 shows a probe 1' according to a second embodiment of the invention. In the probe 1', the channels 14 and the arms 32 are oriented toward the closed anterior end 13 of the tubular body 10. The spring 20 therefore does not rest on this anterior end, but on a narrowing of the lumen or step 15. The actuation of the spring 20 is not obtained by an insertion stylus, but from a cable 52 attached to the sliding part 30: a pulling force exerted on said cable 52 makes it possible to compress the spring 20 and keep the arms 32 in their folded first position, whereas releasing said cable makes it possible for the spring 20 to relax and bring said arms 32 into their unfolded second position. In the case of this second embodiment of the invention, the insertion of the probe 1' could be done using a cannula instead of a stylus. The advantage of this second embodiment of the invention is that the extraction of the probe is much less traumatic than in the first embodiment in case of a failure blocking returning the arms 32 into their folded position.

Of course, in the case of this embodiment it will be necessary to make sure that placing the cable 52 under tension during the introduction of the probe does not cause its buckling. To do this, it is possible to use a rigidification stylus passing through the sliding part 30 and the spring 20 for resting directly on the closed end 13 of the probe. Alternatively, it is possible to perform the insertion using a rigid cannula.

FIG. 7 shows schematically a brain electrostimulation system using a probe 1 according to the first embodiment of the invention, shown in the deployed state inside of the third ventricle V3 of a patient's brain. In a self-evident manner, the tubular body 10 extends through the brain matter MC until leaving the patient's skull by means of an orifice made in the skull of the latter. Matching the posterior end of the tubular body 10, the conducting elements 60 are connected by means of connection 61 to a subcutaneous cable which is in turn connected to an electrical pulse generator for deep neurostimulation 80.

If probe 1 also comprises measurement electrodes, implanted device 80 can also comprise a measurement instrument electrically connected to the latter. In an alternative embodiment, measurement electrodes can be intended for use during the implantation step only (preparatory conditions); in this case, an implanted measurement instrument can be omitted.

The invention was described in reference to a particular embodiment intended for deep brain electrostimulation; however, the invention can be applied more generally to deep electrical neurostimulation of other tissues, such as the spinal cord.

Various structural variants are also conceivable.

For example, the actuation of the arms 32 could be obtained by means other than a spring, for example a shape-memory metal or a piezoelectric actuator. In this case the use of a stylus might not be essential and the insertion could be performed using a rigid cannula.

The arms can comprise more or less than four electrodes; the anterior end part of the tubular body 10 can itself also bear electrodes as in a conventional probe.

Finally, materials different from those explicitly described can be used for the implementation of different components of the invention on the condition that they have suitable mechanical properties and biocompatibility which could be determined without difficulty by the person skilled in the art.

The invention claimed is:

1. A probe (1, 1') for deep electrical neurostimulation comprising:
    a tubular body (10) of biocompatible material with a lateral wall (11) defining a lumen (12), said tubular body (10) being configured to be implanted, for at least a part of a length of the tubular body inside a patient's body for reaching a region to be stimulated;
    a plurality of arms (32) each bearing at least one stimulation electrode (40) and being able to pass from a first position in which they are housed inside of said tubular body (11) to a second position in which they project radially from said lateral wall (11) and inversely; and
    means (20 and 50) for making said arms (32) pass from said first position to said second position and inversely;
    a base element (31) of tubular shape placed inside of the lumen (12) of said tubular body (10);
    wherein a plurality of said arms (32) are connected together by the base element (31), and further wherein said arms (32) and said base element (31) make up a single part (30) of strap shape, wound so as to adapt to the shape of the lumen (12) of said tubular body (10).

2. The probe (1, 1') of claim 1, in which all the arms (32) projecting from said lateral wall (11) from a single axial position ($Z_{301}$ and $Z_{302}$) are connected together by the single tubular-shaped base element (31) placed inside the lumen of said tubular body (10).

3. The probe (1, 1') of claim 1, in which said strap has a thickness between 10 and 100 μm.

4. The probe (1, 1') of claim 3, wherein said strap has a thickness between 12 and 50 μm.

5. The probe (1, 1') of claim 1, in which a plurality of said arms (32) project from said lateral wall (11) from a single axial position ($Z_{301}$, $Z_{302}$).

6. The probe (1) of claim 2 further including a plurality of groups of arms (301 and 302), the arms (32) of each group (301 and 302) projecting from said lateral wall (11) from a single axial position ($Z_{301}$ and $_{302}$) and each of said groups (301, 302) corresponding to a different axial position ($Z_{301}$ and $Z_{302}$).

7. The probe (1, 1') of claim 1, in which said arms (32) are evenly distributed around the lateral wall (11) of said tubular body (10).

8. The probe (1, 1') of claim 1, in which the arms (32) are housed at least in part in channels (14) extending in the lateral wall (11) of said tubular body (10).

9. The probe (1, 1') of claim 8, in which the arms (32) extend in the lateral wall (11) of said tubular body (10) along an oblique direction relative to the axis.

10. The probe (1, 1') of claim 8, in which the means for making said arms pass from said first to said second position include a spring (20) arranged so as to exert on said arms (32) a force directed parallel to the axis of said tubular body (11), so as to push them to the outside through said channels (14).

11. The probe (1, 1') of claim 10, in which said arms (32) are flexible, and are arranged so as to pass from said first to said second position and inversely by translational movement.

12. The probe (1) of claim 10, in which the means to make said arms pass from said second to said first position include a stem (50) which can be actuated in compression for exerting a force opposed to that of said spring (20) so as to make said arms return into said tubular body (11) through said channels (14).

13. The probe (1) of claim 12, in which said stem is a stylus (50) which can be introduced in the lumen (12) of said tubular body (11) to make the tubular body rigid in order for insertion of the tubular body in a patient's body.

14. The probe (1') of claim 10, in which the means to make said arms pass from said second to said first position include a cable (52) which can be actuated in traction for exerting a force opposed to that of said spring (20) so as to make said arms return into said tubular body (11) through said channels (14).

15. The probe (1, 1') of claim 1, in which said arms (32) are made of an electrically insulating material and each have at least one electrode (40) on a respective surface thereof.

16. The probe (1, 1') of claim 15, in which said arms (32) are made, at least in part, from a biocompatible insulating material chosen from the group consisting of polyimides, and in particular polyisoindroquinazorindiones (PIQ) and the polyimide Pi2611, and the benzocyclobutenes (BCB).

17. The probe of claim 1, wherein at least one of said arms also comprises at least a measurement electrode having a smaller surface than that of said stimulation electrodes.

18. The probe of claim 17, wherein a plurality of measurement electrodes are disposed near to each stimulation electrode.

19. The probe (1, 1') of claim 1, including electrically conducting elements (60) extending into the lumen or inside of the lateral wall of said tubular element and forming electrical contacts with the electrodes (40) carried by said arms.

20. The probe (1, 1') of claim 19, in which said electrodes (40) are planar electrodes connected to said electrically conducting elements (60) by means of planar conducting tracks (41) formed on said arms (32).

21. The probe (1, 1') of claim 19, in which said conducting elements (60) extend to an end referred to as posterior of said tubular body (10) and include means of connection (61) to an electrical pulse generator for deep electrical neurostimulation (80).

22. The probe (1, 1') of claim 1, in which said tubular body (10) is made of a biocompatible material chosen from the group consisting of silicones, siloxanes, polyurethane and polyvinyl chloride.

23. The probe (1, 1') of claim 1, in which said tubular body (10) has a substantially cylindrical shape with a diameter between 0.5 and 5 mm.

24. The probe (1, 1') of claim 23, in which said tubular body (10) has a diameter between 0.5 and 2 mm.

25. The probe (1, 1') of claim 1, including a number of arms (32) between 3 and 60.

26. The probe (1, 1') of claim 25, wherein the number of arms (32) is between 4 and 40.

27. The probe (1, 1') of claim 1, in which said arms (32) have a length between 0.2 and 3 mm.

28. The probe of claim 1, wherein the tubular body (10) has a length between 15 cm and 40 cm.

29. A system for deep electrical neurostimulation comprising:
    an electrical pulse generator for deep electrical neurostimulation (80); and
    at least one probe (1) as claimed in claim 1, whose stimulation electrodes are electrically connected to said electrical pulse generator (80).

30. The system of claim 29 wherein at least an arm of said probe comprises at least a measurement electrode having a smaller surface than that of said stimulation electrodes, said system further comprising a measurement instrument electrically connected to said measurement electrodes.

31. The probe (1, 1') of claim 27, wherein said arms (32) have a length between 0.4 and 2 mm.

* * * * *